(12) United States Patent
Haslam et al.

(10) Patent No.: US 11,488,704 B1
(45) Date of Patent: Nov. 1, 2022

(54) PREVENTION AND MITIGATION OF HEALTH EVENTS USING SENSORS AND CONNECTED DEVICES

(71) Applicant: UIPCO, LLC, San Antonio, TX (US)

(72) Inventors: Justin Dax Haslam, San Antonio, TX (US); Christina N. Nickel, Boerne, TX (US); Anthony Scott Farnsworth, San Antonio, TX (US); David John Pflug, San Antonio, TX (US); Kelly Q. Baker, San Antonio, TX (US); Joshua Daniel Elkin, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 120 days.

(21) Appl. No.: 16/543,780

(22) Filed: Aug. 19, 2019

Related U.S. Application Data (60) Provisional application No. 62/725,122, filed on Aug. 30, 2018.

(51) Int. Cl.
*G16H 20/70* (2018.01)
*G16H 50/30* (2018.01)
*G16H 40/63* (2018.01)

(52) U.S. Cl.
CPC ............. *G16H 20/70* (2018.01); *G16H 40/63* (2018.01); *G16H 50/30* (2018.01)

(58) Field of Classification Search
CPC ........ G16H 50/20; G16H 50/30; G16H 40/20; G16H 80/00; G16H 20/70
See application file for complete search history.

(56) References Cited

U.S. PATENT DOCUMENTS

| | | | |
|---|---|---|---|
| 2015/0294086 A1* | 10/2015 | Kare | G16H 20/70 705/3 |
| 2017/0173262 A1* | 6/2017 | Veltz | A61B 5/0022 |
| 2019/0209806 A1* | 7/2019 | Allen | G16H 20/70 |

FOREIGN PATENT DOCUMENTS

| WO | WO-2016145373 A1 * | 9/2016 | .......... A61B 5/0205 |
|---|---|---|---|

OTHER PUBLICATIONS

Diette, Gregory B., et al. "Distraction therapy with nature sights and sounds reduces pain during flexible bronchoscopy: A complementary approach to routine analgesia." Chest 123.3 (2003): 941-948. (Year: 2003).*

* cited by examiner

*Primary Examiner* — Linh Giang Le
*Assistant Examiner* — Constantine Siozopoulos
(74) *Attorney, Agent, or Firm* — Perkins Coie LLP

(57) ABSTRACT

Embodiments described herein disclose technology for detecting and mitigating a health event. The system can monitor health information associated with the user. The health information can be collected by sensors. The system can assess the environment in the location of the user using one or more connected devices and/or sensors. Based on the health information and the environment, the system can detect whether a health event is occurring. In response to detecting a health event, the system can generate a mitigation plan and alter controllable environmental features according to the mitigation plan via the connected devices.

20 Claims, 6 Drawing Sheets

FIG. 6

PREVENTION AND MITIGATION OF HEALTH EVENTS USING SENSORS AND CONNECTED DEVICES

CROSS-REFERENCE TO RELATED APPLICATIONS

This application is a non-provisional of and claims priority to U.S. Provisional Application No. 62/725,122, filed on Aug. 30, 2018, entitled "PREVENTION AND MITIGATION OF HEALTH EVENTS USING SENSORS AND CONNECTED DEVICES," which is hereby incorporated by reference in its entirety for all purposes.

BACKGROUND

Many people experience health events triggered by environmental factors. For example, a person suffering from Post-Traumatic Stress Disorder ("PTSD") can experience stress reactions while watching a movie that reminds the person of the traumatic event, triggering the reaction. Unfortunately, many people endure such health events without immediate support to ease the symptoms.

The techniques introduced here may be better understood by referring to the following Detailed Description in conjunction with the accompanying drawings, in which like reference numerals indicate identical or functionally similar elements. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Many people experience health events triggered by the environment in which the person is subjected. For example, a person suffering from Post-Traumatic Stress Disorder ("PTSD") can have a health event triggered by the temperature, lighting, and/or music. In an example, a violent scene in a movie may trigger a health event, causing the person to sweat and the person's heartrate to rise rapidly. In some instances, the person's health event is not caused by environmental factors. However, in either case, changing the environmental features can assist the user. Many health conditions and particularly mental health conditions (e.g., PTSD) are kept private and left untreated at least in part due to the stigma attached to such conditions.

To address the above-mentioned issues, the technology described herein provides a system and method that detects health events and changes the environment using sensors and devices to ease symptoms without the risk of sending sensitive health information to remote locations where data can be compromised.

In some implementations, a controlling device collects information from sensors that monitor the user's health. The controlling device can be any type of device (e.g., smartphone, tablet, smartwatch) and is preferably in the same environment as the user. Sensors can include cameras (e.g., evaluation of person's physical appearance), heartrate monitor, blood sugar monitor, oxygen level sensor, and thermometer. The controlling device can also detect environmental features from connected devices in the area or sensors. Environmental features can include room temperatures, location, whether the user is indoor or outdoor, content being viewed and/or listened to by the user, time of day, and number of people within a vicinity of the user. In some implementations, the controlling device can act as a connected device and/or a sensor and collect environmental feature information and health information. Such information can be helpful to include in the analysis of whether the user is experiencing a health event. For example, environmental factors can reduce false positives (e.g., the user's heartrate will likely rapidly increase at the gym) or indicate that conditions are likely triggering or going to trigger a health event (e.g., violent content being viewed by the user).

The controlling device analyzes the health information and the environment information to determine whether the user is experiencing a health event. When the controlling device determines that the user is experiencing (or likely going to experience) a health event, controlling device generates a mitigation plan to control controllable environmental features. The controlling device can send messages to various connected devices to change the environment features. For example, the controlling device can send a message to a thermostat to lower the temperature in the room by a few degrees. In some implementations, the controlling device can turn off or edit out violent video content. The mitigation plan may be tiered. For example, the first step may be to send a message to the user. If the user's health information does not show that the symptoms have subsided, the next step may be to dim the lights or shut the blinds via connected devices.

In some embodiments, particularly where the user is in a public environment, permission must be provided to access the connected devices. Permission can be given, for example, via a message (including a doctor's note) that is cryptographically signed and recorded on a distributed ledger, which would keep the user's identity anonymous yet still show proper credentials.

This disclosure describes systems and processes designed to authenticate the person downloading an application and to provide improved device management solutions using unique identifiers for an application. Various embodiments may provide one or more of the following technological improvements: (1) increase security and protection of data by analyzing health and environment locally on a device in the user's environment to detect a health event; (2) increase response time to providing assistance to a user using connected devices; and (3) anonymize requests to change the environment.

In the following description, for the purposes of explanation, numerous specific details are set forth in order to provide a thorough understanding of embodiments of the present technology. It will be apparent, however, that embodiments of the present technology may be practiced without some of these specific details.

Figure 1:
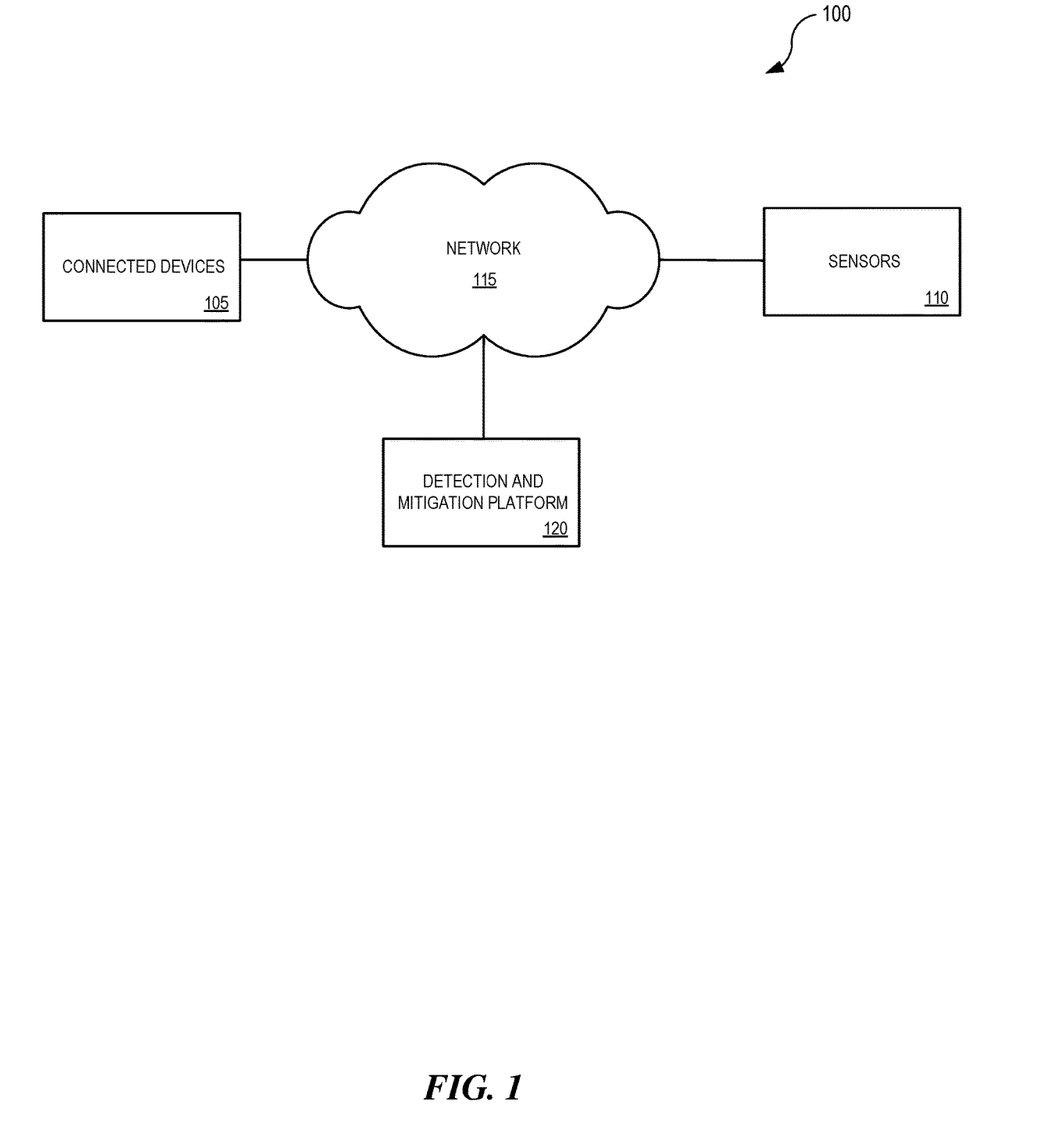
FIG. 1 illustrates an example of a network-based operating environment in accordance with various embodiments of the present disclosure.

FIG. 1 illustrates an example of network-based operating environment 100 in which some embodiments of the present disclosure may be used. As illustrated in FIG. 1, operating environment 100 may include connected devices 105 (e.g., a thermostat, virtual assistant, television, radio, dishwasher, refrigerator, light switch or light dimmer, fan) and sensors 110 (e.g., a heart rate monitor, a thermometer, a wearable, respiration monitor, an oxygen sensor, camera). Various applications can be running on the connected devices 105 or can be stored remotely on a server ("in the cloud"). Connected devices 105 can include mechanisms for receiving and sending traffic by connecting through network 115 to detection and mitigation platform 120.

Connected devices 105 may be configured to communicate via network 115 with detection and mitigation platform 120. In some embodiments, connected devices 105 and sensors 110 can retrieve or submit information to detection and mitigation platform 120. Connected devices 105 can run one or more applications with customized content retrieved by detection and mitigation platform 120. For example, connected devices 105 can execute a browser application or a customized client application to enable interaction between connected devices 105 and detection and mitigation platform 120.

Detection and mitigation platform 120 can be running on one or more servers and can be used to detect and mitigate health events via connected devices 105 and sensors 110, and/or perform other activities. Preferably, detection and mitigation platform 120 is located in the environment of the user. However, in some embodiments, detection and mitigation platform 120 can be a server located remotely from the connected devices 105 and sensors 110.

Network 115 can be any combination of Local Area Networks (LANs) and/or Wide Area Networks (WANs) and use wired and/or wireless communication systems. Network 115 can be or could use any one or more protocols/technologies: Ethernet, IEEE 802.11 or Wi-Fi, worldwide interoperability for microwave access (WiMAX), cellular telecommunication (e.g., 3G, 4G, 5G), CDMA, cable, digital subscriber line (DSL), Bluetooth, Near Field Communications (NFC), etc. Similarly, the networking protocols used on network 115 may include multiprotocol label switching (MPLS), transmission control protocol/Internet protocol (TCP/IP), User Datagram Protocol (UDP), hypertext transfer protocol (HTTP), simple mail transfer protocol (SMTP), and file transfer protocol (FTP). Data exchanged over network 115 may be represented using technologies, languages, and/or formats, including hypertext markup language (HTML) or extensible markup language (XML). In addition, all or some links can be encrypted using conventional encryption technologies such as secure sockets layer (SSL), transport layer security (TLS), and Internet Protocol security (IPsec).

Figure 2:
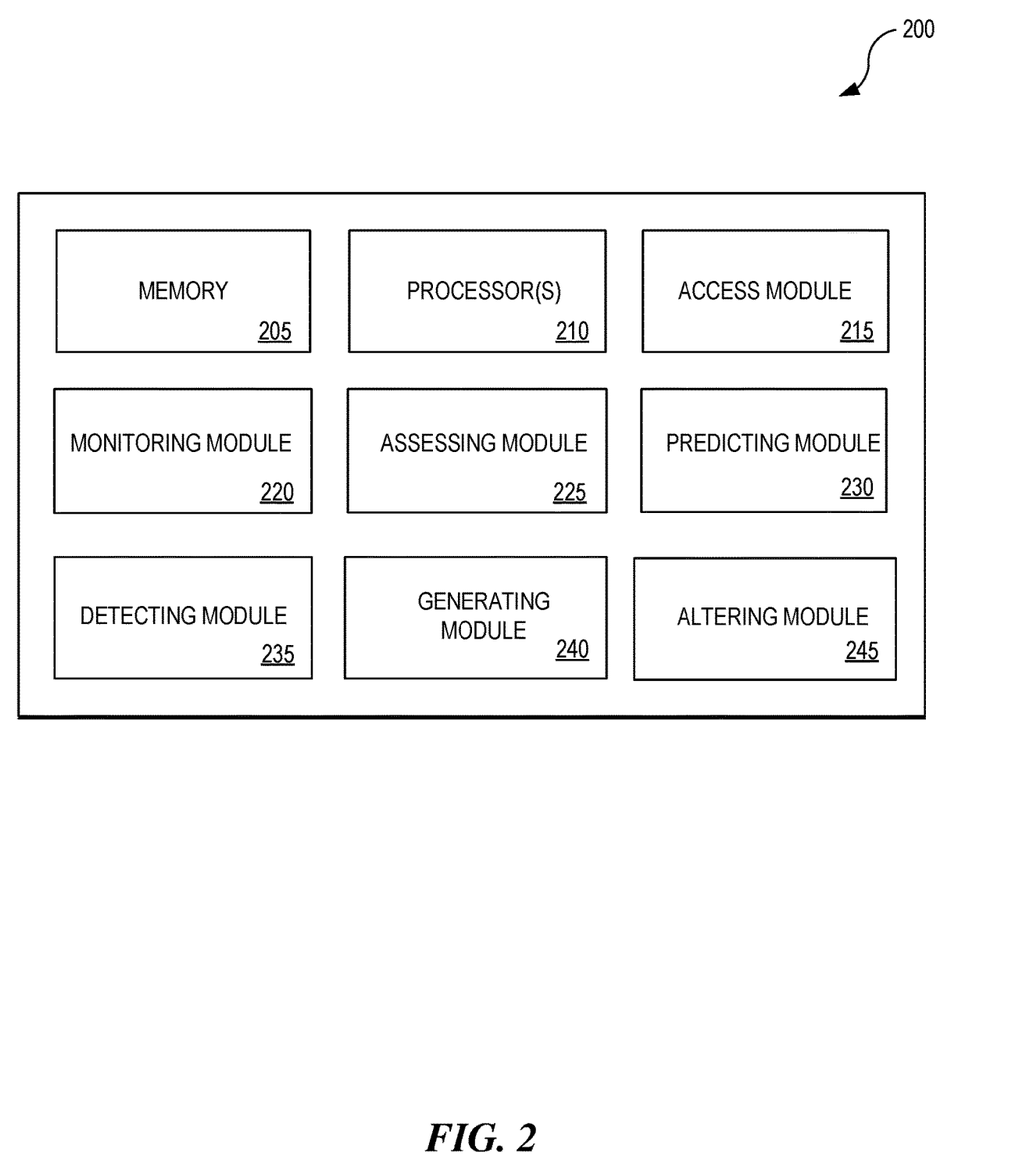
FIG. 2 illustrates various components of a detecting and mitigating platform that can be used in accordance with various embodiments of the present disclosure.

FIG. 2 illustrates a set of components 200 within detection and mitigation platform 120 according to one or more embodiments of the present disclosure. Detection and mitigation platform 120 is generally located in the same environment as the user. While data is collected from many sensors, servers, applications, etc. that are not necessarily in the same environment, most, if not all of the analysis of information is done on detection and mitigation platform 120. This provides a distinct benefit: beyond individual health measurements (e.g., heartrate) being transferred directly from the sensor to detection and mitigation platform 120, the user's health information is generally not transmitted yet the user is receiving immediate assistance. According to the embodiments shown in FIG. 2, detection and mitigation platform 120 can include memory 205, one or more processors 210, access module 215, monitoring module 220, assessing module 225, predicting module 230, detecting module 235, generating module 240, and altering module 245. Other embodiments of the present disclosure may include some, all, or none of these modules and components, along with other modules, applications, and/or components. Still yet, some embodiments may incorporate two or more of these modules and components into a single module and/or associate a portion of the functionality of one or more of these modules with a different module.

Memory 205 can store instructions for running one or more applications or modules on processor(s) 210. For example, memory 205 could be used in one or more embodiments to house all or some of the instructions needed to execute the functionality of access module 215, monitoring module 220, assessing module 225, predicting module 230, detecting module 235, generating module 240, and altering module 245. Generally, memory 205 can include any device, mechanism, or populated data structure used for storing information. In accordance with some embodiments of the present disclosure, memory 205 can encompass, but is not limited to, any type of volatile memory, nonvolatile memory (RAM), and dynamic memory. For example, memory 205 can be RAM, memory storage devices, optical memory devices, magnetic media, floppy disks, magnetic tapes, hard drives, single in-line memory modules (SIMMs), synchronous dynamic random access memory (SDRAM), dual in-line memory modules (DIMMs), Rambus dynamic random access memory (RDRAM), double data rate RAM (DDR RAM), small outline DIMMs (SODIMMs), EPROMs, EEPROMs, compact discs, digital video discs, and/or the like. In accordance with some embodiments, memory 205 may include one or more disk drives, one or more flash drives, one or more databases, one or more tables, one or more files, local cache memories, processor cache memories, relational databases, flat databases, and/or the like. In addition, those of ordinary skill in the art will appreciate many additional devices and techniques for storing information that can be used as memory 205.

Access module 215 can detect connected devices and environmental sensors in an environment and obtain access to these devices to collect data from and/or control the devices. Credentials, doctor's notes, etc. can be required for a controlling device to alter environmental features in some environments such as shared environments (e.g., mall, office). For example, when the controlling device is taken into an environment (e.g., user's home, office), access module 215 can communicate with sensors and connected devices in the environment (e.g., send beacons) and determine access requirements for obtaining information and/or controlling the connected devices. In some implementations, prior to allowing a controlling device to control a connected device, the controlling device can cryptographically sign an access request with the a private key and include evidence that the access needed is for health-related reasons (e.g., a letter by a health care provider) that is recorded on a distributed ledger. Using a distributed ledger can keep the request anonymous and provide provenance.

Monitoring module 220 monitors health information associated with the user collected from sensors. Examples of sensors include a heart rate monitor, a thermometer, a wearable (e.g., Fitbit), respiration monitor, an oxygen sensor, and a blood sugar monitor. Depending on the type of sensor and measurement being taken, the sensors can be connected to the user (heart rate monitor) or can be stationed away from the user (e.g., thermal sensing device, camera).

Assessing module 225 assesses environmental features of the environment in which the user is located using the connected devices and sensors. Examples of the connected devices include a television, a radio, thermostat, a light switch or dimmer, a fan, and a virtual assistant device. In some embodiments, the controlling device can be one of the connected devices to be controlled (e.g., mobile device is playing a movie) and one of the sensors (e.g., mobile device detects room temperature). Sensors can further provide environmental features (e.g., thermometer, number of devices located within a proximity of the user). Examples of environmental factors include temperature, brightness/dimness of lighting, volume of audio or audio-visual device (e.g., television, radio, computer), content of audio-visual device, location (e.g., room in house, type of location such as gym, grocery store, home), and movement (e.g., is the user on a run or bike ride).

Predicting module 230 predicts a likelihood that the user will experience a health event based at least on the environmental features, the user's health history, and the user's current health information. Such information can be sent to generating module 240 to prevent a health event. For example, if the user has historically experienced health events under certain conditions (e.g., room temperature over 80 degrees, violent content being viewed) and the user's heath information indicates the user's heart rate is rising, predicting module 230 can estimate that the user is likely to experience a health event and can alert generating module 240 to develop a plan to prevent the health event.

Detecting module 235 detects a health event based on the health information and the environmental features. To determine whether the health information is indicating a health event, the user's historical health information can be used, including the user's baseline health information and the user's health information when the user experienced previous health events. Detecting module 235 can use the environmental features to reduce false positives. In some embodiments, detecting module 235 determines a probability that the user is experiencing a health event. For example, if assessing module 225 determines that the user is working out at the gym or running outside (e.g., based on location, speed of movement, user feedback, social media), detecting module 235 will calculate a low probability that a health event is occurring even if the user's heartbeat is rapid.

Generating module 240 generates a mitigation plan for the health event in response to receiving information from detecting module 235 that the user is experiencing a health event (or is likely to experience a health event). The mitigation plan can be tailored to the user, the health event, and controllable environmental features. The mitigation plan is communicated to altering module 245 to be carried out. Altering module 245 alters controllable environmental features according to the plan set forth by generating module 240 by, for example, sending instructions to connected devices (e.g., thermostat) or different applications within the same device (e.g., turn off music playing on mobile device).

In an example, after detecting a health event, the mitigation plan can start with sending a simple message to the user with calming words. Next, after a predetermined time, if the user's health information indicates that the user is still experiencing the health event (e.g., symptoms are not improving to at least a certain level), the mitigation plan can include dimming the lights, turning off the television, playing calm music, and turning down the thermostat by a few degrees. Should the user's health information indicate that the user is continuing to experience the health event, the mitigation plan can further include dropping the thermostat by another few degrees. At some point, after all controllable environmental features have been set to the optimal levels for treating the user, if the user continues to experience the health event, the mitigation plan can include sending a message to a trusted person (e.g., doctor, family member), contacting emergency services, or dispensing medication from a controlled medication container.

Those skilled in the art will appreciate that the components illustrated in FIGS. 1-2 described above, and in each of the flow diagrams discussed below, may be altered in a variety of ways. For example, the order of the logic may be rearranged, sub steps may be performed in parallel, illustrated logic may be omitted, other logic may be included, etc. In some implementations, one or more of the components described above can execute one or more of the processes described below.

Figure 3:
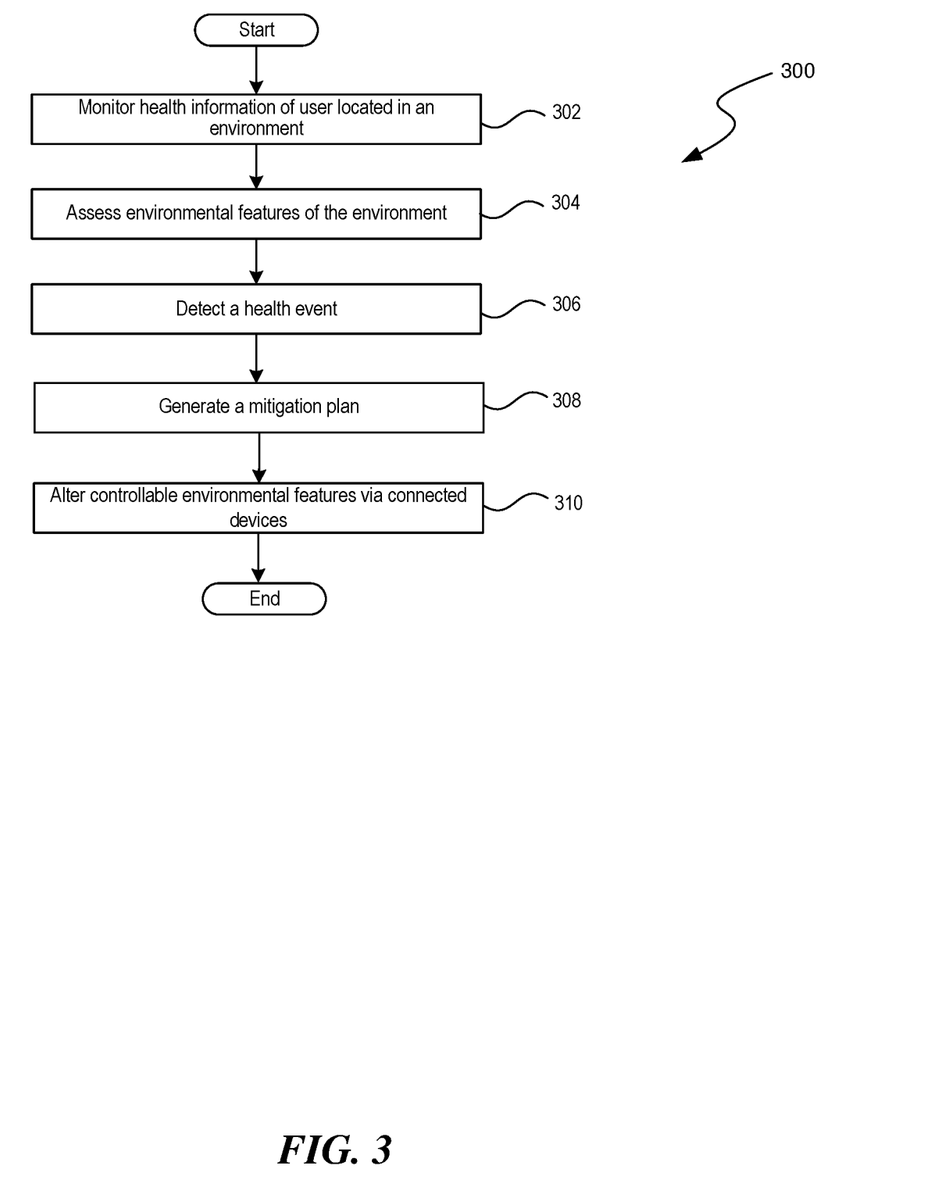
FIG. 3 is a flowchart illustrating a set of operations for detecting and mitigating health events in accordance with various embodiments of the present disclosure.

FIG. 3 is a flow diagram illustrating a process 300 for detecting and mitigating health events. Monitoring operation 302 monitors health information of a user using sensors such as a heartrate monitor. Assessing operation 304 assesses the environmental features of the environment of the user using a plurality of connected devices (e.g., type of content playing on television) and/or services (e.g., weather information from a weather server) and/or sensors (e.g., thermometer, camera). In some implementations, the device monitoring the health information and assessing the environmental features can be one of the connected devices providing information (e.g., location information). Detecting operation 306 detects a health event based on the health information and the environmental features. The environmental features can be used to reduce false positives (e.g., rapid change in heartrate is expected if the user is at the gym). Generating operation 308 generates a mitigation plan for the health event in response to detecting the health event. Altering operation 310 alters controllable environmental factors of the environment of the user according to the mitigation plan. For example, the system can send messages from the device to the connected devices with instructions to change the user's environment. In some embodiments, altering operation 310 sends messages, waits for results from monitoring operation 302, and sends further messages to connected devices when the user is continuing to experience the health event.

Suitable System

Figure 4:
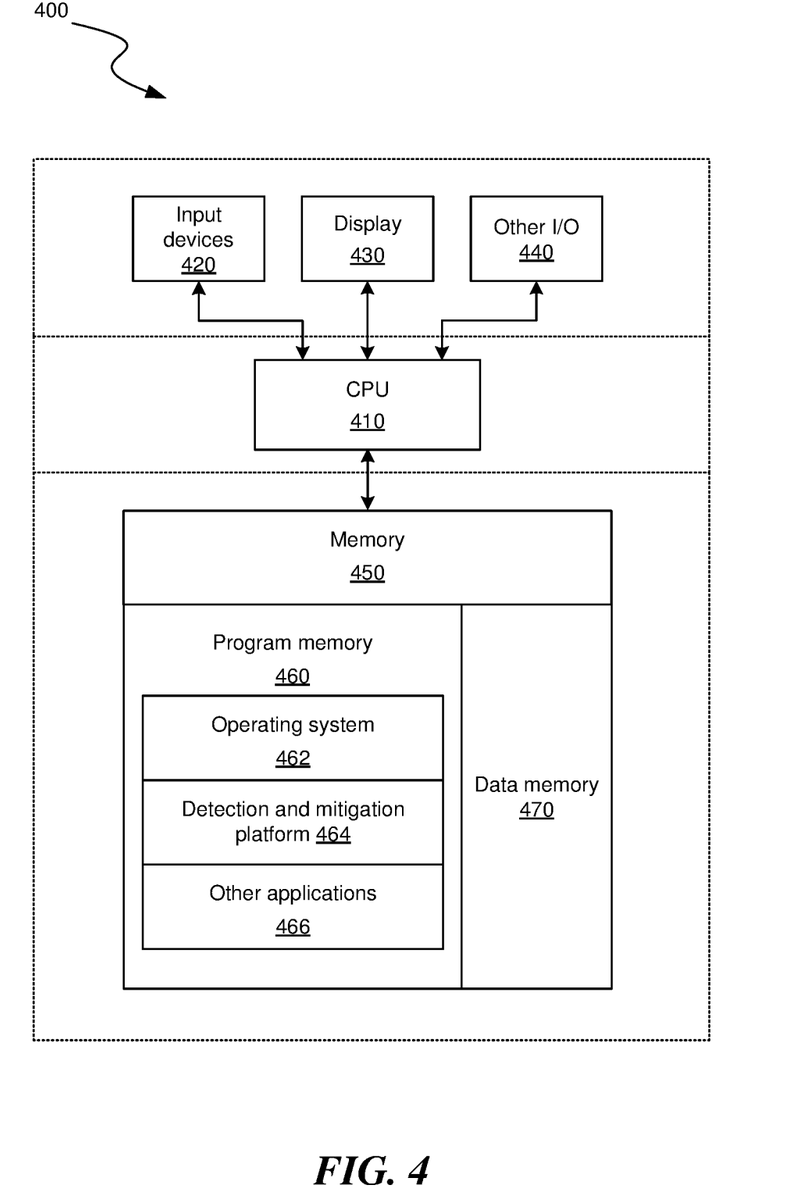
FIG. 4 is a block diagram illustrating an overview of devices on which some implementations can operate.

Several implementations are discussed below in more detail in reference to the figures. Turning now to the figures, FIG. 4 is a block diagram illustrating an overview of devices on which some implementations of the disclosed technology can operate. The devices can comprise hardware components of a device 400 that manage payment card transaction authorizations. Device 400 can include one or more input devices 420 that provide input to the CPU (processor) 410, notifying it of actions. The actions are typically mediated by a hardware controller that interprets the signals received from the input device and communicates the information to the CPU 410 using a communication protocol. Input devices 420 include, for example, a mouse, a keyboard, a touchscreen, an infrared sensor, a touchpad, a wearable input device, a camera- or image-based input device, a microphone, or other user input devices.

CPU 410 can be a single processing unit or multiple processing units in a device or distributed across multiple devices. CPU 410 can be coupled to other hardware devices, for example, with the use of a bus, such as a PCI bus or SCSI bus. The CPU 410 can communicate with a hardware controller for devices, such as for a display 430. Display 430 can be used to display text and graphics. In some examples, display 430 provides graphical and textual visual feedback to a user. In some implementations, display 430 includes the input device as part of the display, such as when the input device is a touchscreen or is equipped with an eye direction monitoring system. In some implementations, the display 430 is separate from the input device. Examples of display devices are: a LCD display screen; a LED display screen; a projected, holographic, or augmented reality display (such as a heads-up display device or a head-mounted device); and so on. Other I/O devices 440 can also be coupled to the processor, such as a network card, video card, audio card, USB, FireWire or other external device, camera, printer, speakers, CD-ROM drive, DVD drive, disk drive, or Blu-Ray device.

In some implementations, the device 400 also includes a communication device capable of communicating wirelessly or wire-based with a network node. The communication device can communicate with another device or a server through a network using, for example, TCP/IP protocols. Device 400 can utilize the communication device to distribute operations across multiple network devices.

The CPU 410 can have access to a memory 450. A memory 450 includes one or more of various hardware devices for volatile and non-volatile storage, and can include both read-only and writable memory. For example, a memory can comprise random access memory (RAM), CPU registers, read-only memory (ROM), and writable non-volatile memory, such as flash memory, hard drives, floppy disks, CDs, DVDs, magnetic storage devices, tape drives, device buffers, and so forth. A memory 450 is not a propagating signal divorced from underlying hardware; a memory is thus non-transitory. A memory 450 can include program memory 460 that stores programs and software, such as an operating system 462, detection and mitigation platform 464, and other application programs 466. A memory 450 can also include data memory 470 that can include user identifying information (e.g., addresses, usernames, passwords, personal identification numbers), baseline health information, historical health information, environment information, contact information for doctors, family, and friends, web browsing history, and other information which can be provided to the program memory 460 or any element of the device 400.

Some implementations can be operational with numerous other general purpose or special purpose computing system environments or configurations. Examples of well-known computing systems, environments, and/or configurations that may be suitable for use with the technology include, but are not limited to, personal computers, server computers, handheld or laptop devices, cellular telephones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like.

Figure 5:
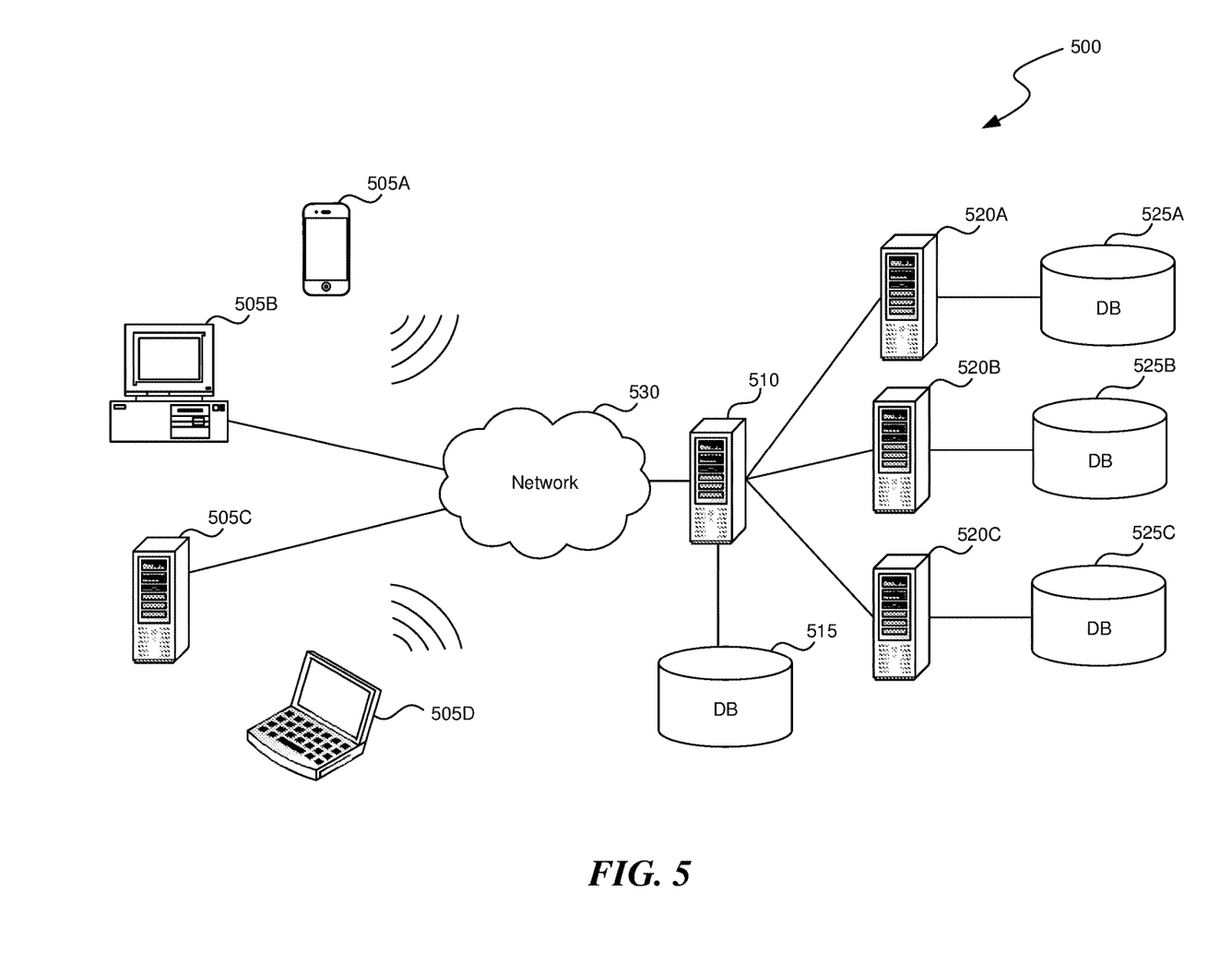
FIG. 5 is a block diagram illustrating an overview of an environment in which some implementations can operate.

FIG. 5 is a block diagram illustrating an overview of an environment 500 in which some implementations of the disclosed technology can operate. Environment 500 can include one or more client computing devices 505A-D, examples of which can include device 400. Client computing devices 505 can operate in a networked environment using logical connections through network 530 to one or more remote computers, such as a server computing device 510.

In some implementations, server computing device 510 can be an edge server that receives client requests and coordinates fulfillment of those requests through other servers, such as servers 520A-C. Server computing devices 510 and 520 can comprise computing systems, such as device 100. Though each server computing device 510 and 520 is displayed logically as a single server, server computing devices can each be a distributed computing environment encompassing multiple computing devices located at the same or at geographically disparate physical locations. In some implementations, each server computing device 520 corresponds to a group of servers.

Client computing devices 505 and server computing devices 510 and 520A-C can each act as a server or client to other server/client devices. Server 510 can connect to a database 515. Servers 520A-C can each connect to a corresponding database 525A-C. As discussed above, each server 520A-C can correspond to a group of servers, and each of these servers can share a database or can have their own database. Databases 515 and 525 can warehouse (e.g., store) information such as health events, contact information, environmental information, connected devices in an environment, permissions to connected devices, and other activity made via an application. Though databases 515 and 525A-C are displayed logically as single units, databases 515 and 525A-C can each be a distributed computing environment encompassing multiple computing devices, can be located within their corresponding server, or can be located at the same or at geographically disparate physical locations.

Network 530 can be a local area network (LAN) or a wide area network (WAN), but can also be other wired or wireless networks. Network 530 may be the Internet or some other public or private network. Client computing devices 505A-D can be connected to network 530 through a network interface, such as by wired or wireless communication. While the connections between server 510 and servers 520A-C are shown as separate connections, these connections can be any kind of local, wide area, wired, or wireless network, including network 530 or a separate public or private network.

Figure 6:
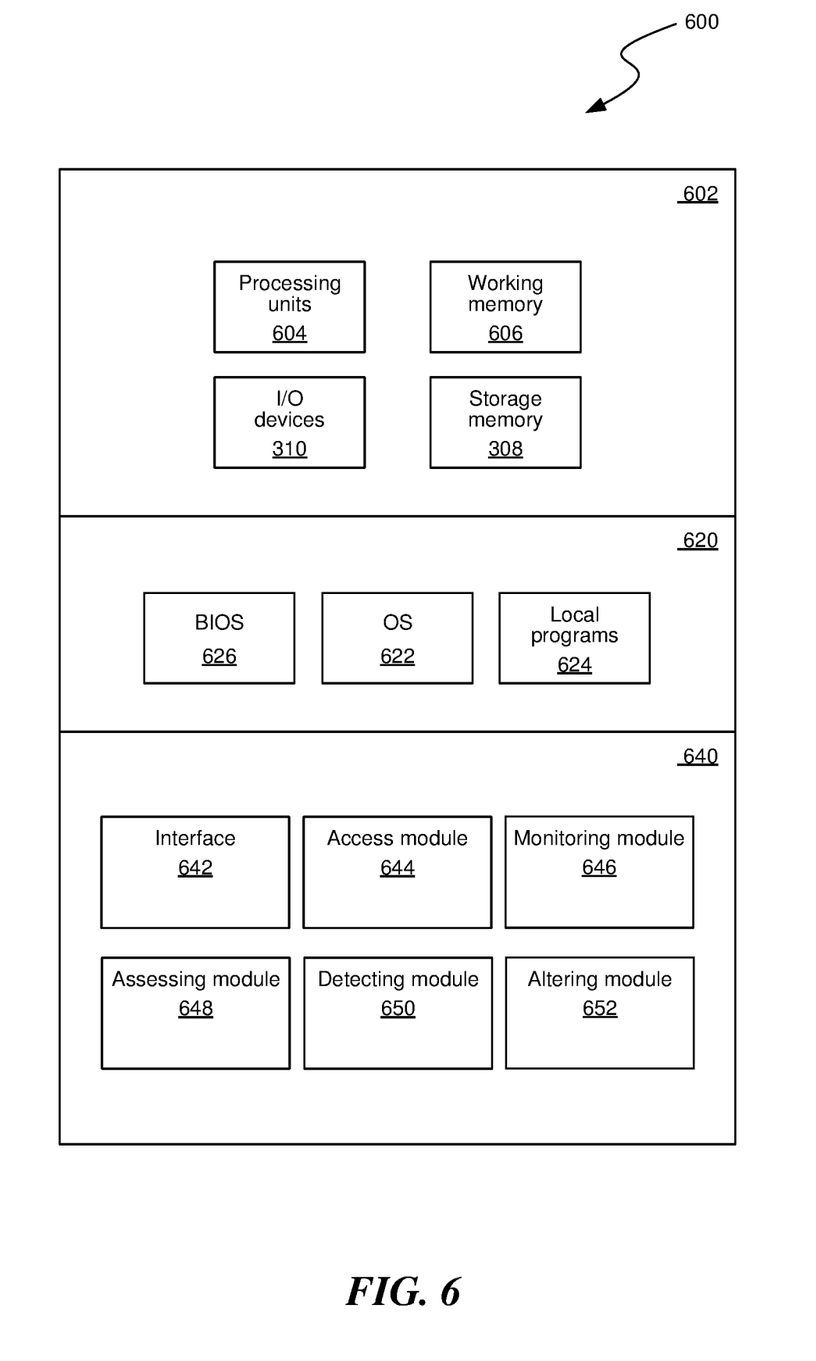
FIG. 6 is a block diagram illustrating components which, in some implementations, can be used in a system employing the disclosed technology.

FIG. 6 is a block diagram illustrating components 600 which, in some implementations, can be used in a system employing the disclosed technology. The components 600 include hardware 602, general software 620, and specialized components 640. As discussed above, a system implementing the disclosed technology can use various hardware, including processing units 604 (e.g., CPUs, GPUs, APUs, etc.), working memory 606, storage memory 608, and input and output devices 610. Components 600 can be implemented in a client computing device such as client computing devices 505 or on a server computing device, such as server computing device 510 or 520A-C. In some embodiments, some components of components 600 can be implemented in a client computing device while others are implemented on a server computing device.

General software 620 can include various applications, including an operating system 622, local programs 624, and a basic input output system (BIOS) 626. Specialized components 640 can be subcomponents of a general software application 620, such as local programs 624. Examples of specialized components 640 include access module 644, monitoring module 646, assessing module 648, detecting module 650, altering module 652, and components that can be used for transferring data and controlling the specialized components, such as interface 642. In some implementations, components 600 can be in a computing system that is distributed across multiple computing devices or can be an interface to a server-based application executing one or more of specialized components 640.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

Several implementations of the disclosed technology are described above in reference to the figures. The computing devices on which the described technology may be implemented can include one or more central processing units, memory, input devices (e.g., keyboards and pointing devices), output devices (e.g., display devices), storage devices (e.g., disk drives), and network devices (e.g., network interfaces). The memory and storage devices are computer-readable storage media that can store instructions that implement at least portions of the described technology. In addition, the data structures and message structures can be stored or transmitted via a data transmission medium, such as a signal on a communications link. Various communication links can be used, such as the Internet, a local area network, a wide area network, or a point-to-point dial-up connection. Thus, computer-readable media can comprise computer-readable storage media (e.g., "non-transitory" media) and computer-readable transmission media.

As used herein, being above a threshold means that a value for an item under comparison is above a specified other value, that an item under comparison is among a certain specified number of items with the largest value, or that an item under comparison has a value within a specified top percentage value. As used herein, being below a threshold means that a value for an item under comparison is below a specified other value, that an item under comparison is among a certain specified number of items with the smallest value, or that an item under comparison has a value within a specified bottom percentage value. As used herein, being within a threshold means that a value for an item under comparison is between two specified other values, that an item under comparison is among a middle specified number of items, or that an item under comparison has a value within a middle specified percentage range.

As used herein, the word "or" refers to any possible permutation of a set of items. For example, the phrase "A, B, or C" refers to at least one of A, B, C, or any combination thereof, such as any of: A; B; C; A and B; A and C; B and C; A, B, and C; or multiple of any item, such as A and A; B, B, and C; A, A, B, C, and C; etc.

The above Detailed Description of examples of the technology is not intended to be exhaustive or to limit the technology to the precise form disclosed above. While specific examples for the technology are described above for illustrative purposes, various equivalent modifications are possible within the scope of the technology. For example, while processes or blocks are presented in a given order, alternative implementations may perform routines having steps, or employ systems having blocks, in a different order, and some processes or blocks may be deleted, moved, added, subdivided, combined, and/or modified to provide alternative or sub combinations. Each of these processes or blocks may be implemented in a variety of different ways. Also, while processes or blocks are at times shown as being performed in series, these processes or blocks may instead be performed or implemented in parallel, or may be performed at different times. Further, any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

We claim:

1. A method comprising:
monitoring, via a device associated with a first user, health information associated with the first user collected from one or more sensors, wherein the first user is located in an environment;
assessing, by the device via one or more connected devices and the one or more sensors, in the environment of the first user, environmental factors of the environment;
detecting, by the device, a stress disorder event based on the health information;
eliminating a false positive of the stress disorder event based on the type of location of the first user and an activity of the first user;
identifying at least one of the environmental factors that triggers the stress disorder event;
generating, by the device, a mitigation plan for the stress disorder event based on the type of environment location of the first user and the at least one of the environmental factors,
  wherein the mitigation plan includes sending a message, based on the type of environment location of the first user, to a second user regarding the stress disorder event of the first user; and
controlling the at least one of the environmental factors that triggers the stress disorder event according to the mitigation plan,
  wherein the device is physically located in the environment.

2. The method of claim 1, wherein the one or more sensors include one or more of: a heart rate monitor, a thermometer, a wearable, respiration monitor, and an oxygen sensor, wherein the one or more connected devices includes at least one of: a television, a radio, thermostat, a light switch or dimmer, a fan, and a virtual assistant device.

3. The method of claim 1, wherein detecting, by the device, the stress disorder event based on the health information and the environment further comprises:
eliminating the false positive of the stress disorder event based at least in part on the environmental factors, wherein the environmental factors include one or more of: location, type of location, indoor or outdoor, temperature, audio content and volume, visual content, audio-visual content and volume, and humidity.

4. The method of claim 1, wherein the device is one of the one or more connected devices.

5. The method of claim 1, wherein the mitigation plan further includes sending, by the device, a message to the user.

6. The method of claim 1, the method further comprising:
after altering the controllable environmental factors of the environment of the user according to the mitigation plan, monitoring the health information of the user;
determining that the stress disorder event is on-going; and
in response to determining that the stress disorder event is on-going, further altering the controllable environmental factors according to the mitigation plan.

7. The method of claim 1, wherein:
the health information is a rapid change in heartbeat,
wherein the environmental factors include a type of audio-visual content,
wherein altering the controllable environmental factors includes, sending via the device a message to the one or more connected devices to turn off the audio-visual content.

8. The method of claim 1, the method further comprising:
prior to altering the controllable environmental factors, obtaining access to the one or more connected devices by cryptographically signing an access request including a letter by a health care provider, wherein the letter is recorded on a distributed ledger.

9. A non-transitory, computer-readable medium comprising a set of instructions that, when executed by a processor, cause the processor to perform operations comprising:
monitoring, via a device associated with a first user, health information associated with the first user collected from one or more sensors, wherein the first user is located in an environment;
assessing, by the device via one or more connected devices and the one or more sensors, in the environment of the first user, environmental factors of the environment;
detecting, by the device, a stress disorder event based on the health information;
eliminating a false positive of the stress disorder event based on the type of location of the first user and an activity of the first user;
identifying at least one of the environmental factors that triggers the stress disorder event;
generating, by the device, a mitigation plan for the stress disorder event based on the type of environment location of the first user and the at least one of the environmental factors,
  wherein the mitigation plan includes sending a message, based on the type of environment location of the first user, to a second user regarding the stress disorder event of the first user; and
controlling the at least one of the environmental factors that triggers the stress disorder event according to the mitigation plan,
  wherein the device is physically located in the environment.

10. The non-transitory computer-readable medium of claim 9, wherein the one or more sensors include one or more of: a heart rate monitor, a thermometer, a wearable, respiration monitor, and an oxygen sensor, wherein the one or more connected devices includes at least one of: a television, a radio, thermostat, a light switch or dimmer, a fan, and a virtual assistant device.

11. The non-transitory computer-readable medium of claim 9, wherein the detecting, by the device, the stress disorder event based on the health information and the environment further comprises:
eliminating the false positive of the stress disorder event based at least in part on the environmental factors, wherein the environmental factors include one or more of: location, type of location, indoor or outdoor, temperature, audio content and volume, visual content, audio-visual content and volume, and humidity.

12. The non-transitory computer-readable medium of claim 9, wherein the device is one of the one or more connected devices.

13. The non-transitory computer-readable medium of claim 9, wherein the operations further comprise sending, by the device, a message to the user in accordance with the mitigation plan.

14. The non-transitory computer-readable medium of claim 9, wherein the operations further comprise:
after altering the controllable environmental factors of the environment of the user according to the mitigation plan, monitoring the health information of the user;
determining that the stress disorder event is on-going; and in response to determining that the stress disorder event is on-going, further altering the controllable environmental factors according to the mitigation plan.

15. The non-transitory computer-readable medium of claim 9,
wherein:
the health information is a rapid change in heartbeat,
wherein the environmental factors include a type of audio-visual content,
wherein altering the controllable environmental factors includes, sending via the device a message to the one or more connected devices to turn off the audio-visual content.

16. The non-transitory computer-readable medium of claim 9, wherein the operations further comprise:
prior to altering the controllable environmental factors, obtaining access to the one or more connected devices by cryptographically signing an access request including a letter by a health care provider, wherein the letter is recorded on a distributed ledger.

17. A system comprising:
a data store for storing a set of instructions; and
at least one processor in communication with the data store, wherein the processor executes the set of instructions that cause the processor to perform operations comprising:
monitoring, via a device associated with a first user, health information associated with the first user collected from one or more sensors, wherein the first user is located in an environment;
assessing, by the device via one or more connected devices and the one or more sensors, in the environment of the first user, environmental factors of the environment;
detecting, by the device, a stress disorder event based on the health information;
eliminating a false positive of the stress disorder event based on the type of location of the first user and an activity of the first user;
identifying at least one of the environmental factors that triggers the stress disorder event;
generating, by the device, a mitigation plan for the stress disorder event based on the type of environment location of the first user and the at least one of the environmental factors,
wherein the mitigation plan includes sending a message, based on the type of environment location of the first user, to a second user regarding the stress disorder event of the first user; and
controlling the at least one of the environmental factors that triggers the stress disorder event according to the mitigation plan,
wherein the device is physically located in the environment.

18. The system of claim 17, wherein the environmental factors includes a number of devices detected within a proximity of the user.

19. The system of claim 17, wherein the device is one of the one or more connected devices.

20. The system of claim 17, wherein the operations further comprise: prior to altering the controllable environmental factors, obtaining access to the one or more connected devices by cryptographically signing an access request including a letter by a health care provider, wherein the letter is recorded on a distributed ledger.

\* \* \* \* \*